US008538119B2

(12) United States Patent
Taki et al.

(10) Patent No.: US 8,538,119 B2
(45) Date of Patent: Sep. 17, 2013

(54) PARTICLE IMAGE ANALYSIS METHOD AND APPARATUS

(75) Inventors: Miki Taki, Hitachinaka (JP); Norio Oowada, Naka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 450 days.

(21) Appl. No.: 12/996,114

(22) PCT Filed: May 12, 2009

(86) PCT No.: PCT/JP2009/058866
§ 371 (c)(1),
(2), (4) Date: Dec. 14, 2010

(87) PCT Pub. No.: WO2009/147931
PCT Pub. Date: Dec. 10, 2009

(65) Prior Publication Data
US 2011/0090247 A1  Apr. 21, 2011

(30) Foreign Application Priority Data
Jun. 4, 2008  (JP) ................................. 2008-146980

(51) Int. Cl.
*G06K 9/00* (2006.01)
(52) U.S. Cl.
USPC ....................................................... 382/133
(58) Field of Classification Search
USPC ................... 382/100, 128, 133, 134; 356/39, 356/335, 441; 250/222.2
See application file for complete search history.

(56) References Cited

U.S. PATENT DOCUMENTS

| 5,715,182 A | 2/1998 | Asai et al. ...................... 364/555 |
| 5,721,433 A | 2/1998 | Kosaka ......................... 250/573 |
| 5,880,835 A * | 3/1999 | Yamazaki et al. ............. 356/336 |

FOREIGN PATENT DOCUMENTS

| JP | 60-38653 A | 2/1985 |
| JP | 4-72544 A | 3/1992 |
| JP | 7-113738 A | 5/1995 |
| JP | 8-136439 A | 5/1996 |
| JP | 8-210961 A | 8/1996 |
| JP | 2006-118899 A | 5/2006 |

OTHER PUBLICATIONS

M. Taki, 7. Nyo Kensa to Sentan Gijutsu 6800-kei Hitachi Nyo Jido Bunseki Sochi, Gekkan Medical Technology separate volume Shin Color Atlas Nyo Kensa, Sep. 20, 2004, pp. 143-149.

* cited by examiner

*Primary Examiner* — Andrew W Johns
(74) *Attorney, Agent, or Firm* — Mattingly & Malur, PC

(57) ABSTRACT

A particle image analyzing method is adapted so that while raising image-reviewing efficiency at a cropped image level of particle components in a sample, the entire sample can be observed without significantly changing a related apparatus configuration. Prior to image reviewing of an imaging region, cropped images thereof are reviewed and, with reference to the images arranged for each kind of particle component, if the operator judges any particles to have been falsely identified, the operator uses an operating unit to modify positions of the particles to those of correct component items. An overall image of the imaging region is displayed and if any components to be added (overlooked components) appear, the kinds of these components are identified and quantitative data on each kind of component is registered. Upon completion of the registration, the concentration of the sample is recalculated and a comment is entered in a comment field.

14 Claims, 13 Drawing Sheets

FIG.5
(A)
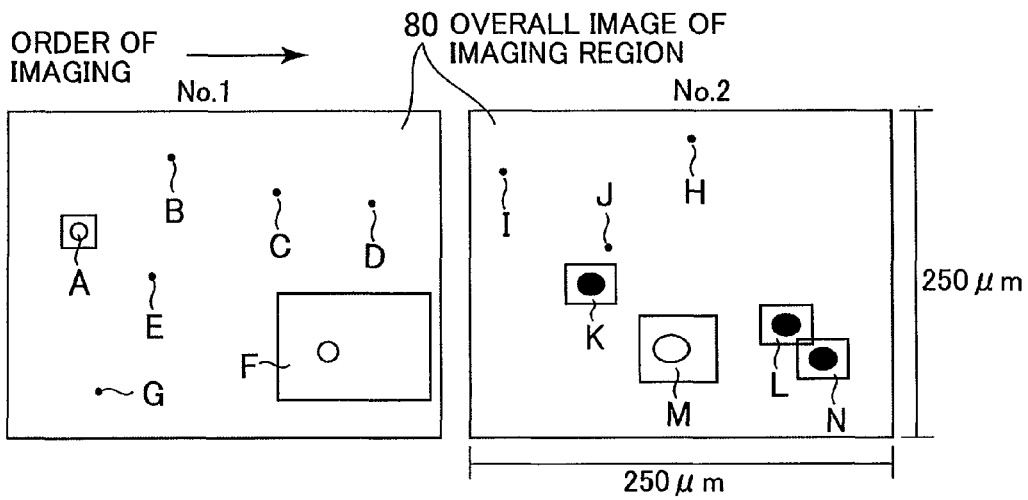
(B)
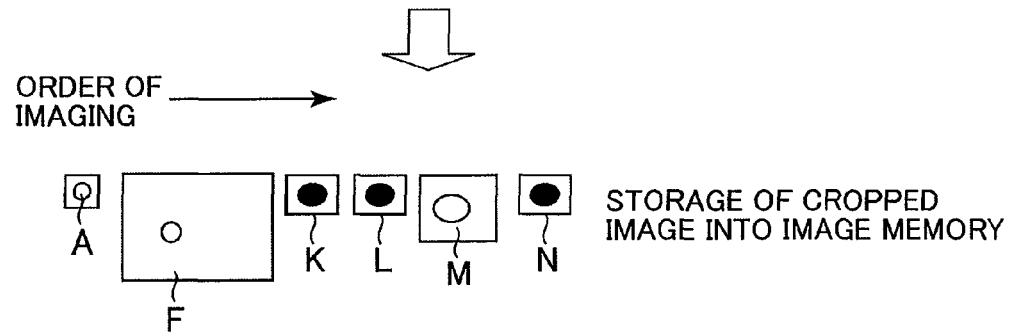
STORAGE OF CROPPED IMAGE INTO IMAGE MEMORY
(C)
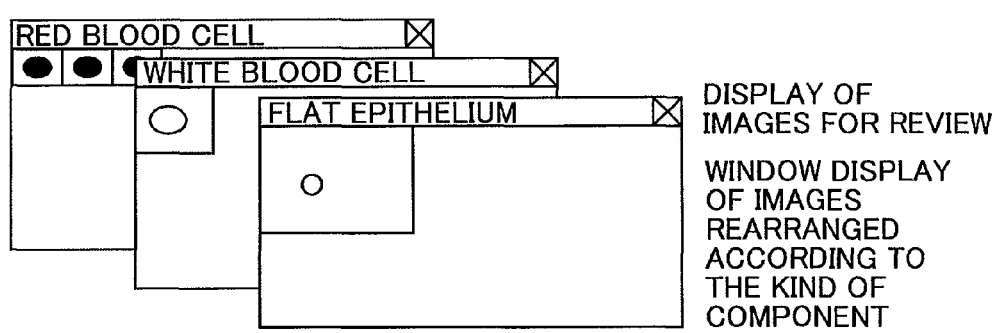
DISPLAY OF IMAGES FOR REVIEW
WINDOW DISPLAY OF IMAGES REARRANGED ACCORDING TO THE KIND OF COMPONENT <EXAMPLE OF REGISTERING COMPONENT ID, NUMBER, AND REGION>

FIG.12

| REGION OVERALL IMAGE ACQUISITION CONDITIONS SETUP | ☒ |
|---|---|

| PARTICLE DETECTION COUNT? | 500 PIECES |
| AMOUNT OF IMAGE DATA TO BE ACQUIRED | 200 IMAGES |

| QUALITATIVE ITEM? | BACTERIAL ▼ |
| IMAGE DATA TO BE SAVED? | 3 IMAGES |

CANCEL    REGISTER

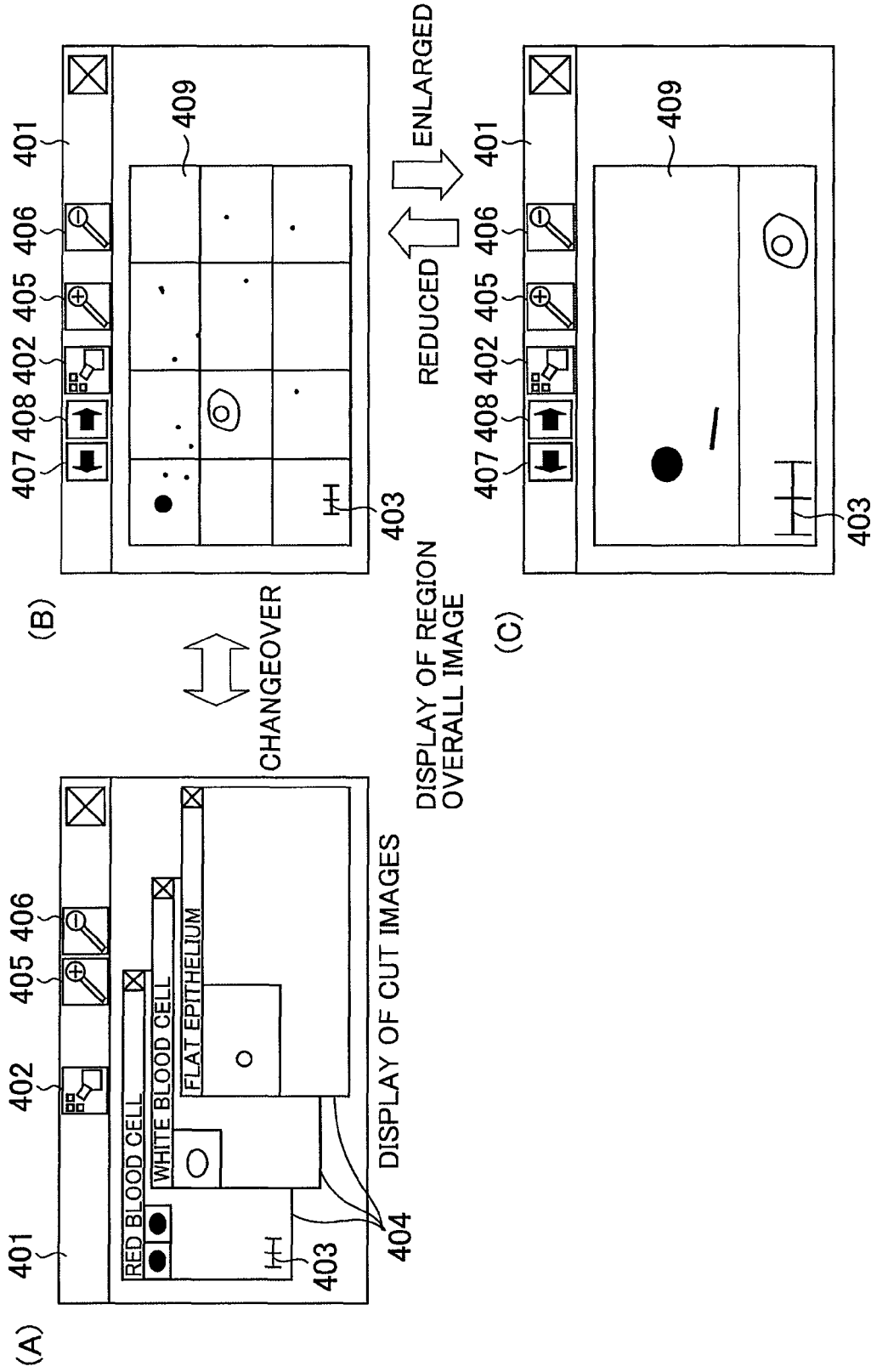

PARTICLE IMAGE ANALYSIS METHOD AND APPARATUS

This application is the national stage of International Application No. PCT/JP2009/058866, filed May 12, 2009.

TECHNICAL FIELD

The present invention relates to a method and apparatus for acquiring images of particles suspended in a liquid, and analyzing the particles from the acquired images.

BACKGROUND ART

To implement labor saving and highly accurate testing when classifying and analyzing the cells existing in a biological sample such as blood, urine, body fluid, or tissue fluid, Patent Document 1, for example, proposes a flow-type particle image analyzing apparatus that uses a flow cell to render the sample fluid a very flat flow shrouded with a cleaning agent acting as a sheath fluid.

In the conventional flow-type particle image analyzing apparatus, the sample that moves through the flow cell is imaged with a video camera, for example, and acquired still video images undergo processing for classifying/counting the particles contained in the sample.

In addition, Patent Document 2 describes a flow-type image analyzing apparatus that employs a method in which acquired images of particles are divided according to particle size or the like, then displayed on a screen, and further classified by an operator.

Furthermore, Patent Document 3 describes a method in which, when an operator classifies particles, a function that reviews only a previously designated kind of component is provided, thereby reducing the reviewing time required.

PRIOR ART REFERENCES

Patent Documents

Patent Document 1: JP-4-72544-A
Patent Document 2: JP-60-38653-A
Patent Document 3: JP-8-210961-A

SUMMARY OF THE INVENTION

Problems to be Solved by the Invention

In the flow-type particle image analyzing apparatus described in Patent Document 2, reviewing efficiency is enhanced by collectively displaying images for each kind of component. The detection limits of the particle image analysis that are of greater importance, however, remain unchanged, and for reasons such as the difficulty with discrimination from contamination (dirt) and other problems associated with classification accuracy, components as small as about 1 to 2 micrometers are excluded from the image-based particle analysis. For a urine test, for example, cocci, a small species of bacteria, are unavoidably excluded from the test since the cocci cannot be analyzed from the size of an image. Additionally, if amorphous salts are appearing on the sample, the influence of the salts will usually spread to the entire background. Cropped images, however, will only contain or provide fragmentary information and will not enable the entire sample to be viewed. Since small components cannot be analyzed, automatic classification is likely to lead to wrong measurement results.

Furthermore, some kinds of particles may be falsely identified as artifacts distinct from biological components in terms of feature parameters. In such a case, these particle components will not remain in the form of an image, and a possibility that very rare biological components have been discarded cannot be denied, either.

For particle imaging, setting small particle components as particles to be imaged leads to imaging contamination (dirt) and other unnecessary components wastefully and thus to reducing the accuracy of detection and classification. It is appropriate, therefore, that detection levels for image acquisition be at least 3 μm, a size that enables distinction from contamination (dirt). However, since, as discussed above, particles smaller than 3 μm are excluded from imaging, bacteria and other small particles in an image cannot be disadvantageously imaged.

Laboratory technicians are trained so that for understanding an overall image of a sample during a routine laboratory test, they can detect a failure by viewing the entire sample on a slide at a low magnification and checking particle information of salts, bacteria, and others, against empirical data. However, laboratory technicians have limits to detection accuracy of a failure only with reference to images for which the component section is separated.

For example, with an image analyzing apparatus, even small components can be classified by, for example, raising the magnification optically, but since large (50-micrometer or larger) components cannot be assayed simultaneously, the image analyzing apparatus needs to have an assay mode that changes the magnification. This will increase time and costs, losing the analyzer in the meaning of existence as a routine test apparatus for the clinical tests that require rapidity. In particular, with an apparatus that exclusively tests urine as a sample, it is difficult to raise the magnification since diverse components are mixedly present in the sample.

In addition, since urinary sediment tests are morphologic tests, it is difficult, partly from a clinical standpoint, to process all samples at the apparatus side, so in these tests, automatic classification is adopted as primary screening, and detailed classification is conducted as secondary screening based on image reviewing. Image reviewing itself has its limits and at least a part of the samples will eventually be subjected to microscopical examination. Even after introduction of an analyzing apparatus, if a number of samples are to be subjected to microscopical examination, the expenditure incurred therefor, including personnel expenses, will double. It is strongly desired, therefore, that the number of samples to be subjected to microscopical examination be minimized.

At the locations of imaging-based urinary test apparatuses, currently about 30% of samples are generally subjected to microscopical examination. A test substance that needs to be subjected to microscopical examination involves centrifuging first and then sample preparation before the substance can be examined through the microscope.

An object of the present invention is to realize a method and apparatus for analyzing particle images, adapted so that while raising image-reviewing efficiency at a cropped image level of particle components in a sample, components as small as or smaller than an imaging region can be observed on an overall image of the sample without significantly changing a related apparatus configuration.

Means for Solving the Problems

In order to achieve the above objects, aspects of the present invention are constructed as follows:

A particle image analyzing method includes: acquiring a sample; storing an acquired overall image of the sample into an overall-image memory; extracting particle components contained in the sample, and number of the particles, from the acquired overall image of the sample; analyzing the extracted particle components in accordance with feature parameters, then after classifying the particle components according to the kind of component, computing respective concentrations of the classified components, and storing the classified components with the computed concentrations into a cropped image memory; displaying on display means the overall image stored in the overall-image memory; and in accordance with to-be-added or to-be-changed particle component information entered from operating means, conducting modifications and concentration-modifying computations upon the components stored in the cropped image memory.

In addition, a particle image analyzing apparatus includes: means for imaging a sample; an overall-image memory for storage of an overall image of the sample acquired by the imaging means; a particle analyzer that extracts the number of particle components contained in the sample from the acquired overall image of the sample; a feature extractor that extracts the particle components contained in the sample from the acquired overall image of the sample; an arithmetic processor which, in accordance with feature parameters, analyzes the particle components extracted by the feature extractor, then classifies the particle components according to the kind of component, and computes respective concentrations of the classified components; a cropped image memory for storage of the classified particle components and the concentrations thereof; display means that displays the overall image stored in the overall-image memory; operating entry means for entering particle component information to be added or changed; and a result-modifying processor which, in accordance with the to-be-added or to-be-changed particle component information entered from the operating entry means, conducts modifications and concentration-modifying computations upon the components stored in the cropped image memory.

The apparatus also includes, in an upstream section of an imaging region, means for detecting the particles passing through the means, and means for using a resulting detection signal to determine whether the particles are to be imaged. The apparatus sets a plurality of conditions for detecting particles, and uses one of particle detection stages to acquire images. Each time a particle passes through, the particles detected at each of the stages are counted during an assay of the sample. The apparatus further includes logic to calculate the respective counts and differences or ratios between the counts, thereby to determine whether overall image acquisition is to be executed, the number of images to be acquired, and whether overall image display is to be conducted, and the number of images to be displayed.

Effects of the Invention

According to the present invention is realized a particle image analyzing method and apparatus adapted so that while raising image-reviewing efficiency at a cropped image level of particle components in a sample, components as small as or smaller than an imaging region can be observed on an overall image of the sample without significantly changing the apparatus configuration.

BRIEF DESCRIPTION OF THE DRAWINGS

FIG. 5 is an explanatory diagram of a process in which acquired images are re-acquired as cropped images for reviewing;

FIG. 12 is a diagram that shows an example of an operating screen for setting the number of overall images to be saved; and FIG. 13 is a diagram that shows an example of a display select screen for selectively displaying an overall image and cropped images of the imaging region.

MODE FOR CARRYING OUT THE INVENTION

Hereunder, embodiments of the present invention will be described referring to the accompanying drawings.

First Embodiment

Figure 1:
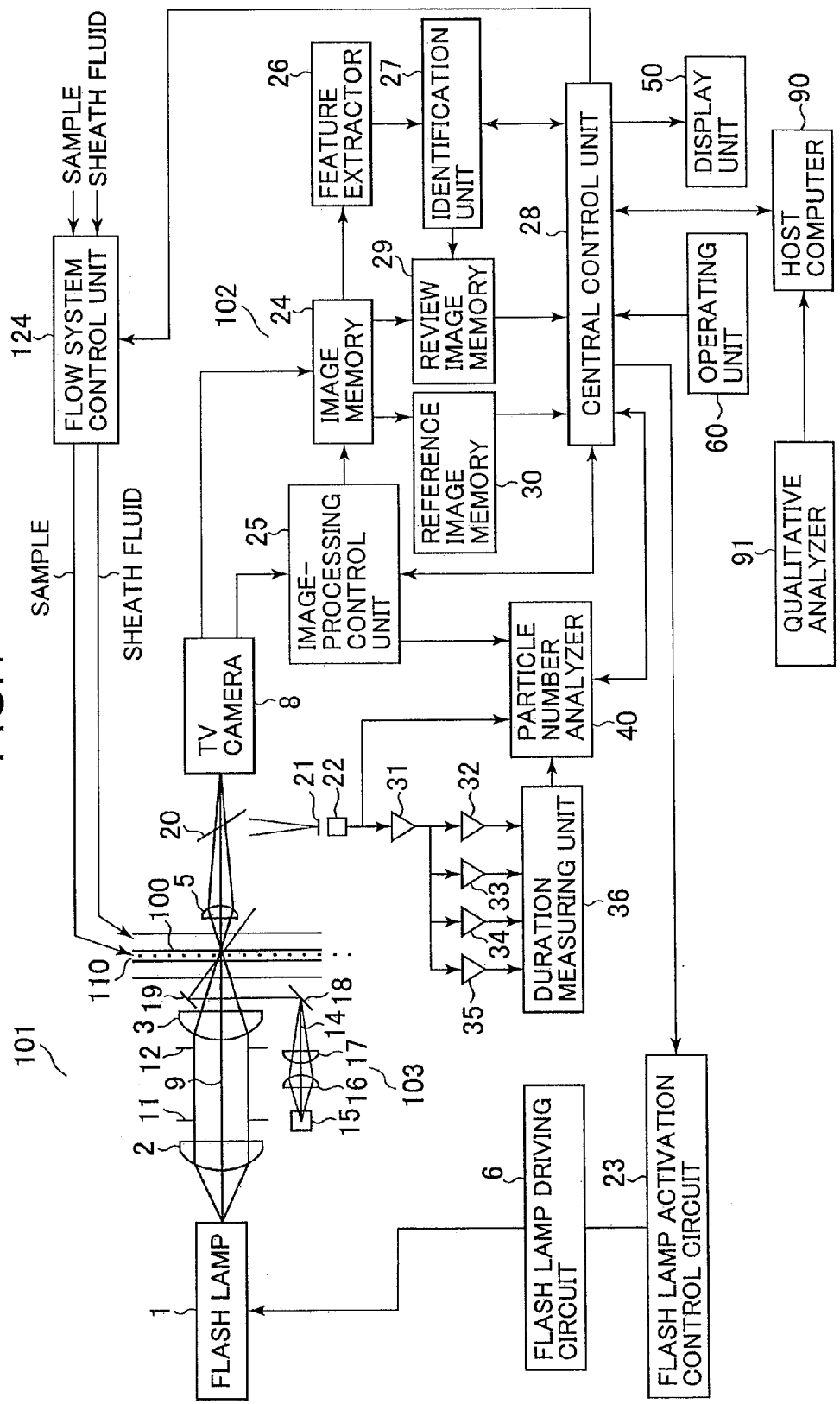
FIG. 1 is an overall schematic block diagram of a flow-type particle image analyzing apparatus which is a first embodiment of the present invention.

FIG. 1 is an overall schematic block diagram of a flow-type particle image analyzing apparatus which is a first embodiment of the present invention. The flow-type particle image analyzing apparatus in FIG. 1 includes a flow cell 100, an imaging block 101, a particle analyzing block 102, a particle detection block 103, and a flow circuit control unit 124.

The imaging block 101 includes a flash lamp driving circuit 6, a flash lamp 1, a field lens 2, a field stop 11, an aperture stop 12, a microscope condenser lens 3, a microscope objective lens 5 (also used as the particle detection block 103), and a TV camera 8. The particle analyzing block 102 includes an image memory 24, an image-processing control circuit 25, a feature extraction circuit 26, an identification circuit 27, a particle number analyzer 40, a central control unit 28, a particle image memory 29 for reviewing, a display unit 50, and an operating unit 60. The central control unit 28 is connected to a qualitative analyzer 91 via a host computer 90. Analyses by the qualitative analyzer 91 are acquired via the host computer 90 by the central control unit 28 and then used for determining qualitative items from acquired image data.

The particle detection block 103 includes a semiconductor laser source 15, a collimator lens 16, a cylindrical lens 17, a reflecting mirror 18, a micro-reflecting mirror 19, a beam splitter 20, a stop 21, a photodetection circuit 22, and a flash lamp activation control circuit 23, in addition to the microscope objective lens 5 mentioned above.

Laser light from the semiconductor laser source 15 is collimated into parallel beams 14 of laser light by the collimator lens 16, and after reaching the reflecting mirror 18, the light irradiates a particle detection region 70 (shown in FIG. 2) within the flow cell 100 via the micro-reflecting mirror 19 disposed between the microscope lens 3 and the flow cell 100.

Figure 2:
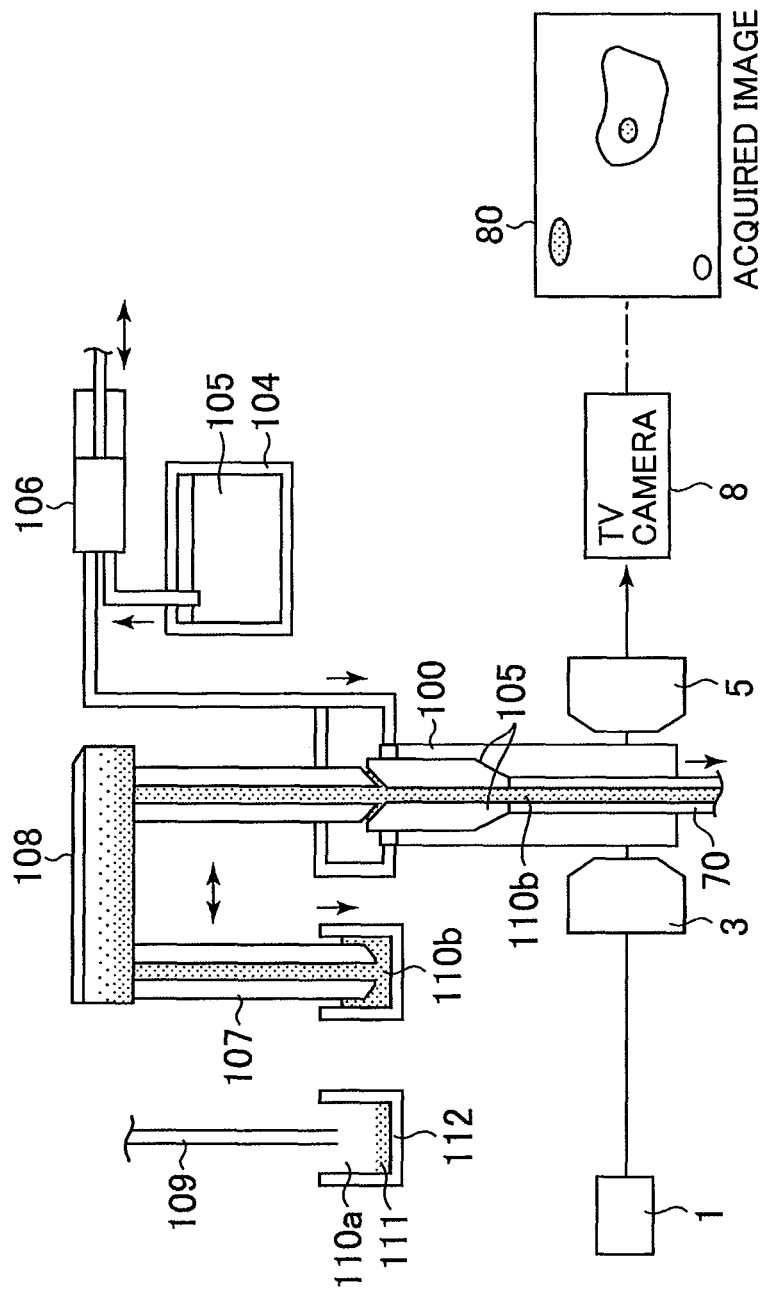
FIG. 2 is an explanatory diagram mainly of a flow cell in the flow-type particle image analyzing apparatus configuration.

FIG. 2 is an explanatory diagram mainly of the flow cell 100 in the apparatus configuration. Operational flow control of the apparatus is described below using FIG. 2. Referring to FIG. 2, a sampling nozzle 109 acquires a sample 110a by suction, and discharges the sample 110a into a dyeing tank 112 from which a dye solution 111 has been discharged beforehand. Next after elapse of a fixed time, a direct-sampling nozzle 107 of a direct-sampling mechanism 108 acquires a dye sample 110b from the dyeing tank 112 by suction, and injects the dye sample 110b into the flow cell 100. At this time, the apparatus injects a sheath fluid 105 from a sheath fluid container 104 into the flow cell 100 while holding the dye sample 110b from both sides with a syringe mechanism 106. For this reason, an entrance for the sheath fluid to enter the flow cell 100 is divided into two sections.

In addition, in the flow cell 100, thickness of the dye sample in a measuring flow pathway is controlled according to a particular ratio of flow rates of the dye sample 110b and the sheath fluid 105. For example, if the flow rate of the dye sample 110b is constant, when the flow rate of the sheath fluid 105 decreases, the very flat flow of the dye sample increases in thickness while maintaining constant width. When the flow rate of the sheath fluid 105 increases, the very flat flow of the dye sample decreases in thickness while maintaining constant width.

To analyze urinary formed elements, the flow cell 100 needs to be 200 to 350 micrometers wide, since sizes of the elements range between several micrometers and 200 micrometers. Thickness forms a flat sample flow that ranges nearly between several micrometers and several tens of micrometers. The particle imaging region 70 is of a square shape, having substantially the same length per side as the width of the flow of the sample. An image 80 obtained will measure about 250 to 300 micrometers in width and length.

Referring back to FIG. 1, the particle detection block 103 further includes an analyzing unit adapted to detect passage of particles and whether imaging is to be executed, and to measure the number of particles at each of plural levels. When the particles of the sample 110 that are to be counted run through the beams of laser light, the laser light is scattered and the scattered light is collected by the microscope objective lens 5 used for particle imaging. Next, the collected light is reflected by the half mirror 20, and then after passing through the stop 21, the light is converted into an electrical signal by the photodetector 22 and a photodetection circuit 31. Upon reaching a specific detection level or more, each particle signal that has thus been converted into the electrical signal form has its duration measured by one of digital output level detection circuits 32, 33, 34, 35 and a duration measuring unit 36. The laser light source 15 is normally in an activated condition, always monitoring the internal particles of the sample passing through the detection region. When detection signals from the photodetection circuit 22 reach a predefined level and predefined pulse width, the corresponding particles are judged to be the particles to be imaged, and these particles are counted by the particle number analyzer 40. Additionally, under control by the central control unit 28, the flash lamp 1 is activated in such timing that the imaging of the particles is stopped at a defined position in an image acquisition field by the flash lamp activation control circuit 23 and the flash lamp driving circuit 6. The particles within the flow cell 100 are then detected and the image 80 is acquired by the imaging block 101.

This particle judgment logic is provided in plurality, and the level detection circuits 32 to 35 accept different detection level settings. When the level settings are exceeded and predefined pulse widths are exceeded, the particle number analyzer 40 counts the corresponding particles.

At the particle analyzing block 102, image data signals output from the TV camera 8 are each stored into a required address of the image memory 24 under control of the image-processing circuit 25. The data that has thus been stored into the image memory 24 is read out under the control of the image-processing control circuit 25, then after being input to the identification circuit 27 via the feature extraction circuit 26, the data undergoes image processing, and results are supplied to the central control unit 28. The results supplied are particle classification results and the particle identification feature parameter data that has been used for the particle classification.

Particle classification/identification logic is automatically executed by a pattern recognition process that is usually performed. These image-processing results, measuring conditions, and image information that has been obtained as a result of image processing are transmitted from the central control unit 28 to the particle analyzer 40. Under the control signals from the central control unit 28, the particle detection signals from the photodetection circuit 22, and the control signals from the image-processing control circuit 25, the particle analyzer 40 examines association between the detected particles and the particle classification results, and compiles final classification/identification results on the particle images. The compiled results are returned to the central control unit 28 and when necessary, output to the display unit 50 for display.

Meanwhile, for particle image reviewing, an operator first selects a desired kind of particle from the operating unit 60. This selection is conveyed to the identification circuit 27 via the central control unit 28, and only when the classification/identification results by the identification circuit 27 match a name of the particle to be reviewed, the corresponding particle images are sent from the image memory 24 to the review image memory 29 and sequentially stored into the memory 29.

The review image memory 29 is provided exclusively for storage of the particle images to be reviewed. After the counting of the particles in the sample, the particle images stored into the review image memory 29 are sent therefrom to the central control unit 28, then displayed on a display screen of the display unit 50, for each kind of particle, and reviewed by the operator.

Based on these measurement results, a calculation of the particle concentrations in the sample and a calculation of particle quantities per field are conducted and analytical results are returned to the central control unit 28.

Figure 3:
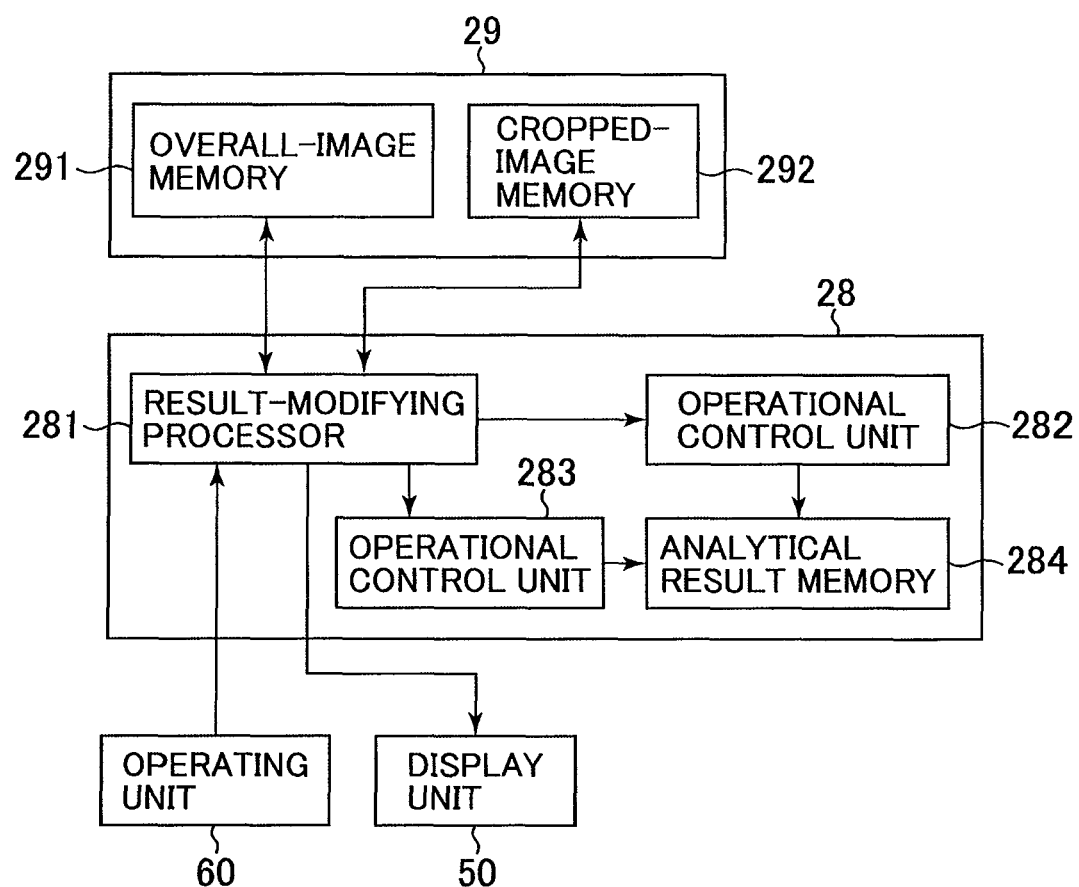
FIG. 3 is an explanatory diagram of internal functional blocks between a review image memory and a central control unit.

FIG. 3 is an explanatory diagram of internal functional blocks between the review image memory 29 and the central control unit 28.

The review image memory 29 in FIG. 3 includes an overall-image memory 291 and a cropped image memory 292. In addition, the central control unit 28 includes a result image-modifying processor 281 which, in accordance with operating commands from the operating unit 60, acquires images from the overall-image memory 291 and the cropped image memory 292 and modifies the images, an arithmetic processor 283 that computes data in accordance with commands from the result-modifying processor 281, an analytical result memory 284 for storage of the analytical results that have been processed by the arithmetic processor 283, and an operational control unit 282 that controls operation of the display unit 50 and other constituent elements of the apparatus. After measurement, measurement results are sent to the host computer 90. The apparatus further includes an element that receives test results from the host computer 90 before the measurement, these test results having been obtained from the same sample by the urinary qualitative analyzer 91 using a test paper method.

Figure 4:
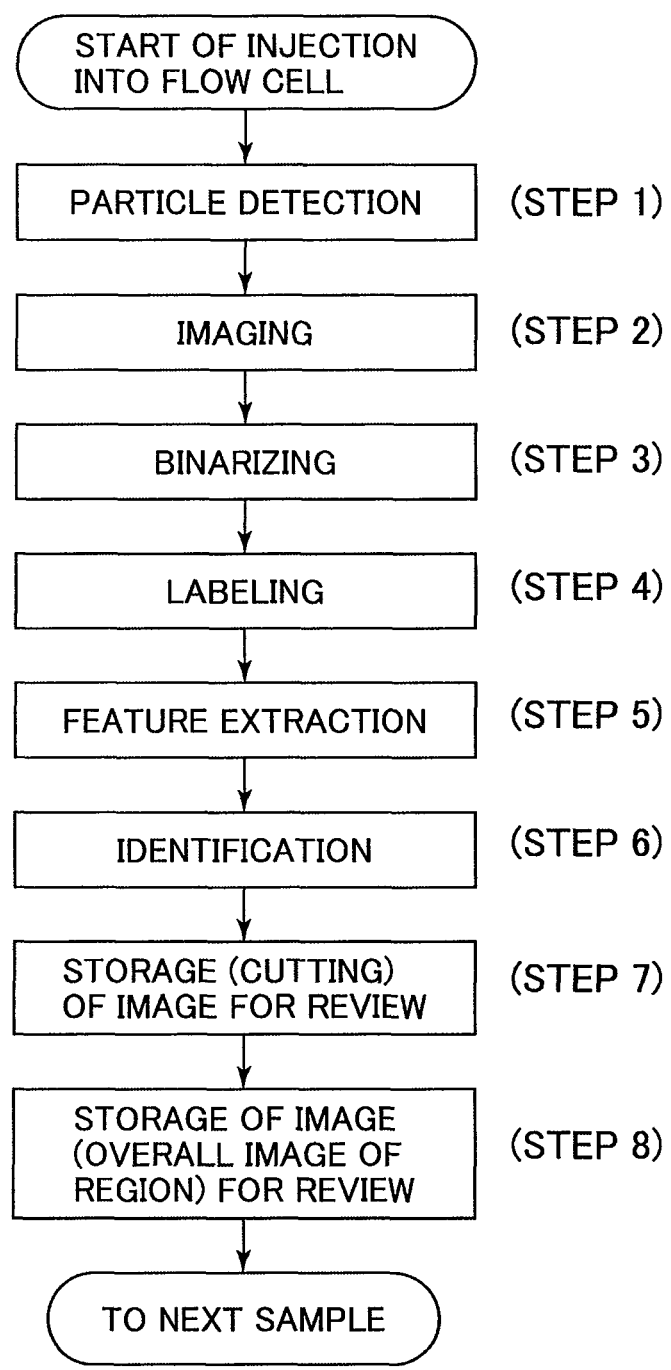
FIG. 4 is an overall process flowchart of particle analysis.

Next, an overall process flow of the particle analysis in the first embodiment of the present invention is described below using FIG. 4. Referring to FIG. 4, the injection of the dye sample 110b into the flow cell 100 is started first. Upon being detected in the particle detection block 103 (Step 1), particles are imaged by the TV camera 8 (Step 2). After this, the image-processing control circuit 25 separates each acquired image 80 into a background and components, that is, binarizes the image (Step 3). Next, the components that have been obtained by the separation are each coded, that is, labeled (Step 4).

After that, a size, color information, a degree of circularity, and other feature parameters are calculated for each component (Step 5). At this time, small components (less than 3 micrometers) are excluded from the calculation. The remaining images have their particle components identified from the feature parameters, on a neural network basis (Step 6). The identified images are each cut into a component area only, assembled as a review image for each kind of component, and stored into the cut memory 292 of the review image memory 29 (Step 7). At a final phase of the measurement, an arbitrarily preset number of images of the entire imaging region are acquired and then stored into the overall-image memory 291 of the review image memory 29 (Step 8).

The above is the process flow from image processing to storage into the review image memory 29.

Next, the process flow of acquiring obtained images as cropped images for review is described below referring to FIG. 5. Each component in the images of the entire imaging region is coded in order of imaging, as shown in section (A) of FIG. 5. The coding is equivalent to labeling Step 4 in the flowchart of FIG. 4.

Small particle components B, C, D, E, G, I, J, and H are dimensionally excluded from processing, and particle components A, F, K, L, M, and N are stored as cropped images into the cropped image memory 292. These images are subjected to later reviewing, which is equivalent to Step 7 in FIG. 4. The images are rearranged according to the kind of component (red blood cells, white blood cells, flat epithelia, or the like), and each kind of component is displayed on an independent window as shown in sections (B) and (C) of FIG. 5.

Next, image-reviewing methods for modifying measurement results of the same sample from an overall image of an imaging region in the present invention are described below using FIGS. 6 and 7. The process in which, during measurement, not only cropped images, but also images of the entire imaging region are stored according to particular settings, is added in the first embodiment of the present invention.

Figure 6:
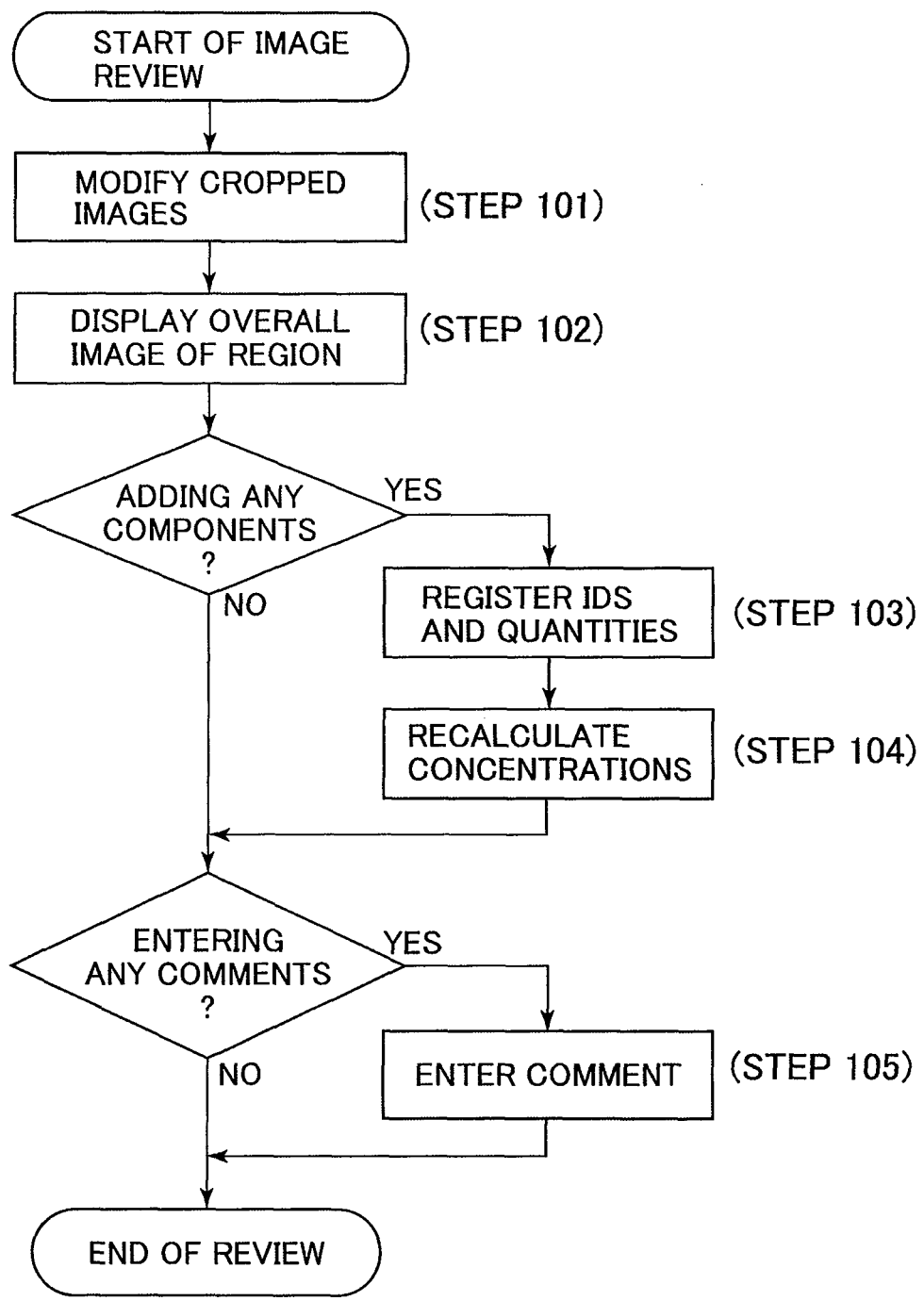
FIG. 6 is a process flowchart that shows an image-reviewing method for modifying measurement results of the same sample from an overall image of an imaging region, the method being applied to a case in which components to be added are present.
Figure 7:
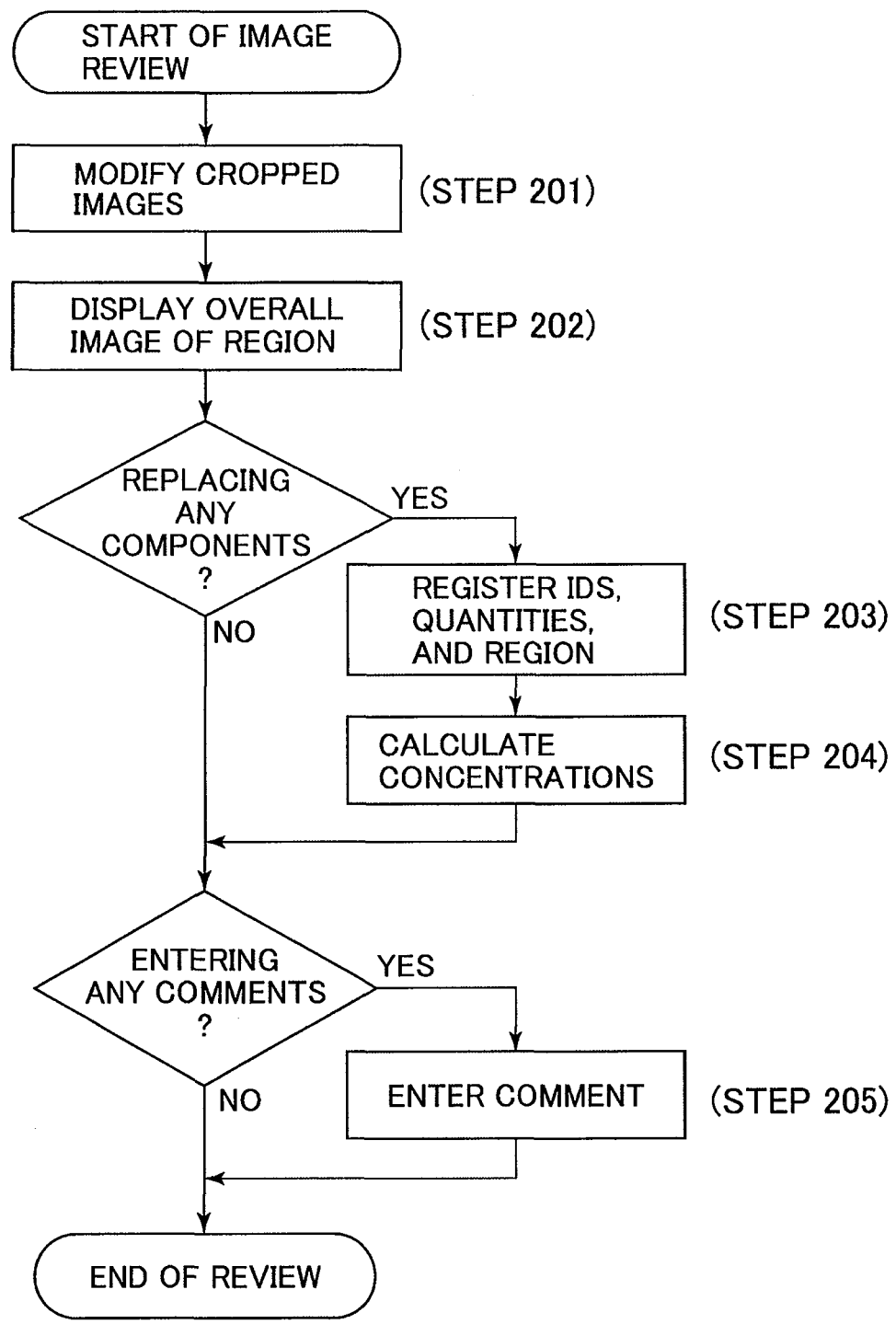
FIG. 7 is a process flowchart that shows an image-reviewing method for modifying measurement results of the same sample from an overall image of an imaging region, the method being applied to a case in which components are distributed in the entire sample and measurement results on the components are to be replaced.

FIG. 6 is a process flowchart that applies to a case in which components to be added are present, and FIG. 7 is a process flowchart that applies to a case in which components are distributed in the entire sample and measurement results on the components are to be replaced. During measurement, overall images of the imaging region can be acquired for saving. Therefore, these images may be separated from the images intended for classification, or the images that have been or were used for the classification may be used for display.

In FIG. 6, prior to image reviewing of the entire imaging region, cropped images are reviewed first (Step 101). In accordance with instructions of the operator from the operating unit 60, the result-modifying processor 281 conducts the review by reading out these images from the cropped image memory 292 and displaying the images on the display unit 50. The images that have been arranged according to the kind of component undergo operator's checks for false identification results. If the operator judges any particles to have been falsely identified, the operator uses the operating unit 60 to modify positions of the particles to those of correct component items. If a relationship between a measured volume and number indicates presence of concentration information in each image, moving the image will also move the corresponding concentration information. For example, if a measuring capacity is 5 microliters and 10 red blood cells are detected, simple calculation with a correction coefficient and other factors missed out leads to a red blood cell concentration of 10 pieces/5 microliters=2 pieces/microliter. Since 10 cells are detected, a 0.2 piece/microliter is contained in one image. This concentration information indicates a concentration of one red blood cell.

If one of the ten red blood cells which the apparatus has identified is modified into a white blood cell by the operator, a concentration of white blood cells increases by 0.2 piece/microliter. In this manner, modifications are conducted according to a movement of the concentration information contained in one cropped image. This means that if one red blood cell is modified into a white blood cell, the red blood cell concentration of 2.0 pieces/microliter and white blood cell concentration of 1.0 piece/microliter in the unreviewed state of the image will be modified to a red blood cell concentration of 1.8 pieces/microliter and a white blood cell concentration of 1.2 pieces/microliter, respectively, in the image existing after being reviewed.

An overall image of the imaging region is next displayed (Step 102). The result-modifying processor 281 reads out this image from the overall-image memory 291 and sends the image to the display unit 50 for display. The operator observes the displayed overall image, then if any components to be added (i.e., overlooked components) exist in the image, locates/identifies the components, and registers the number thereof (Step 103). After the registration, the concentrations of the sample are recalculated by the arithmetic processor 283 (Step 104).

For example, if one renal tubular epithelial cell is detected and this cell is to be added, since the measuring capacity as a whole is 5 microliters, unless that component is present in a cropped image, a concentration of 0.0 piece/microliter in the unreviewed image state and a concentration of 1 piece/5 microliters=0.2 piece/microliter in the image existing after being reviewed will be added as new information to analytical results. Whether the component has been classified needs to have been discriminated on screen display.

In other words, the result modification for adding one renal tubular epithelial cell is conducted so that the renal tubular epithelial cell concentration of 0.0 piece/microliter in the unreviewed image state will be 0.2 piece/microliter in the image existing after being reviewed.

Finally, if, during the review of the imaging region's overall image, information on the sample, in addition to concentration information, is to be transmitted to a clinical jobsite, the operator enters a comment (e.g., a name of probable or likely bacterium) in a comment field via the operating unit 60 (Step 105).

Processing in the case that components are distributed in the entire sample is described below using the process flowchart of FIG. 7. Cropped image modification (Step 201) and comment entry (Step 205) are substantially the same as the operations in Steps 101 and 105 of FIG. 6.

The case in which components are distributed in the entire sample means a case in which the bacteria and amorphous salts dimensionally excluded from the analysis on a cropped image can be observed on an overall image of the imaging region, that is, the case where the small components (B, C, D, E, G, H, I, and J) excluded in the example of FIG. 5 can be observed on an overall image of the imaging region.

After the cropped image modification in Step 201 of FIG. 7, an overall image of the imaging region is displayed (Step 202). For example, if bacteria can be observed on the entire image and are distributed in the entire sample, a process for replacing concentrations of components is conducted. An area of the imaging region and thickness information on the sample are contained in the overall image 80 (shown in FIG. 8) of the imaging region beforehand. A region is designated on the display unit 50 via the result-modifying processor 281 by use of a mouse, a stylus pen, or the like, of the operating unit 60. The operator conducts a screen discrimination of the designated region 301 in FIG. 8, and after identifying positions of components in the region, enters the positions and number information from the operating screen (Step 203). The central control unit 28 then uses the result-modifying processor 281 and the arithmetic processor 283 to calculate measurement results on the components and stores the results into the analytical result memory 284 for replacement (Step 204).

Figure 8:
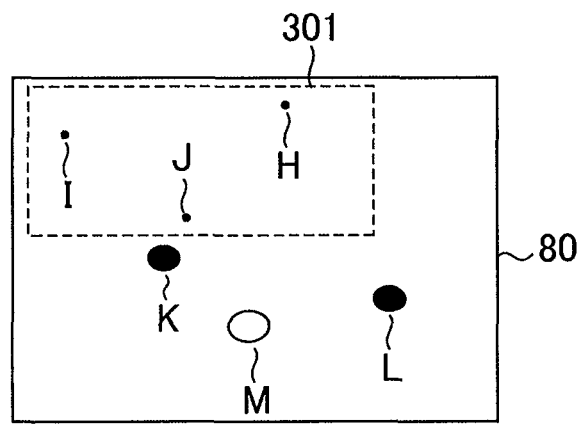
FIG. 8 is an explanatory diagram of an operating screen for replacing image review results and a component concentration.

FIG. 8 is an explanatory diagram of the operating screen for replacing a concentration of a component. The operator determines the region 301 on the overall image 80 of the imaging region in FIG. 8 by dragging the mouse. The arithmetic processor 283 calculates a volume V of the selected region 301 from the thickness of the dye sample 110*b* in the flow cell 100 and an area of the region. An ID of the component is selected from a pull-down menu, in an "ID?" field on the operating screen shown in FIG. 8.

Additionally, entering a number in a "Number?" field on the operating screen of FIG. 8 and then pressing a register (registration) button activates the arithmetic processor 283 to calculate the concentration and replace existing measurement results. For example, if the calculation is conducted assuming that three bacteria (H, I, and J) are present in the designated region and that the volume of the designated region is 0.1 microliter, the concentration will be 3.00 pieces/0.1 microliter=30 pieces/microliter.

If an element for specifying the entire screen as a desired region is also provided and a plurality of images can be set, detection sensitivity can be further enhanced.

That is to say, the result modification for replacing the concentration of a bacterium is conducted so that a concentration of 0.0 piece/microliter in the unreviewed image state will be 30.0 pieces/microliter in the image existing after being reviewed.

As described above, the first embodiment of the present invention enables the operator to confirm presence of components to be added, by saving an overall image of an imaging region independently of the images cut for each kind of component, reading out the overall image of the imaging region, and confirming the entire imaging region that has been read out.

Thus, the present invention realizes the particle image analyzing method and apparatus adapted so that while raising image-reviewing efficiency at the cropped image level of the particle components in the sample, the entire sample can be observed without significantly changing the apparatus configuration.

Second Embodiment

Hereunder, a second embodiment of the present invention will be described.

The flow-type particle image analyzing apparatus described above includes the particle detection block 103, which, when the particles in the sample pass through the flow cell 100, detects a detection level and if this detection level exceeds a constant level, activates the flash lamp 1 to start the acquisition of images.

For a urine sample, the urine is normal if the number of particle components therein is small. However, as the number of components detected increases, small components are more likely to be detected at the same time. It is unnecessary to confirm one specific imaging region on all samples by acquiring an overall image of the imaging region. If the overall image is acquired for each sample, this will increase the memory capacity required and reviewing all stored overall images will require a long time, thus preventing test efficiency from being raised.

In the second embodiment of the present invention, therefore, threshold values based on level-by-level particle detection counts and detection durations are provided and if the threshold values are exceeded during measurement, the preset number of overall images are acquired only for that sample. The second embodiment also includes a constituent element that uses either the particle counts at the plurality of detection levels or ratios of these counts to determine whether overall images are to be acquired and/or displayed.

The kinds of urinary formed elements are diverse and detection signal levels and widths of these elements also vary. The problem is how small microparticles should be imaged. The components imaged need to be discriminated from contamination (dirt) and noise in terms of detection signal states, but very small components of the same level as that of contamination (dirt) and noise appear during operation. The cocci in urine are particularly difficult to discriminate from contamination (dirt) and noise. If even such microparticles are imaged just by reason that they cannot be discriminated, image data will increase too much for the apparatus to implement accurate classification and efficient processing. Since the current apparatus is intended for the components measuring about 3 μm or more, the cocci that are appearing may be overlooked.

Figure 9:
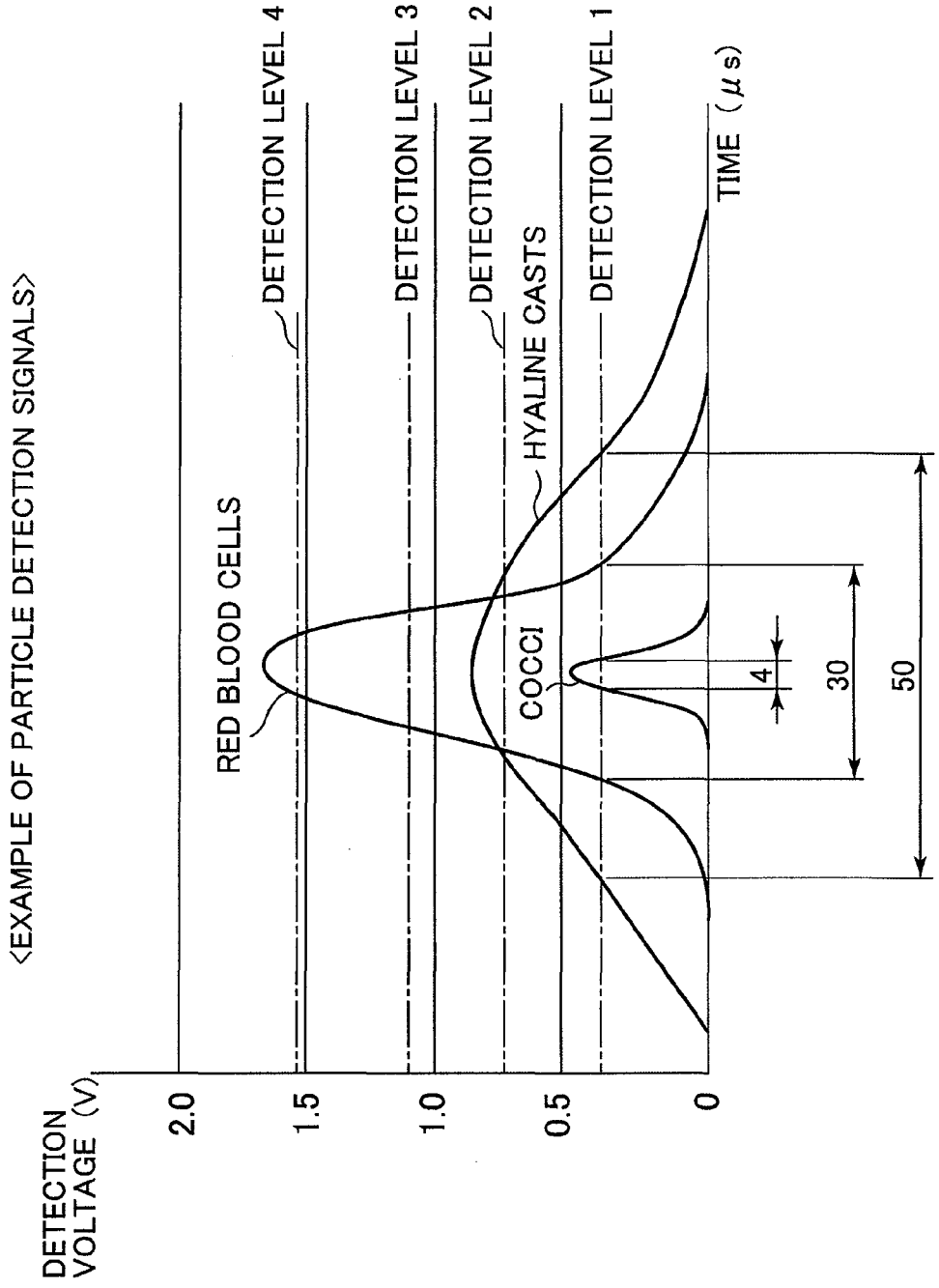
FIG. 9 is a diagram that shows an example of particle detection signals.

FIG. 9 shows an example of particle detection signals in urinary formed elements. A horizontal axis denotes a detection duration (μs), and a vertical axis denotes a detection voltage (V). Larger particles need a longer time to pass through, so these particles require a longer duration. The detection voltage tends to increase as an internal density and other values of the particle become high. Cocci of 1-2 μm in diameter are small in signal level and width. Red blood cells, compared with cocci, exhibit high voltage levels at diameters of 6-8 μm. Since the internal contents that are 50-100 μm wide hyaline casts have low densities, the hyaline casts are relatively low in detection level, but at the same time, the hyaline casts also feature a long detection duration. Red blood cells can be classified on an image basis, so the threshold values for the components to be imaged are set to be at least 2 in detection level and at least 30 µs in detection duration. Level settings of the components to be imaged can be changed just by changing the detection level.

Figure 10:
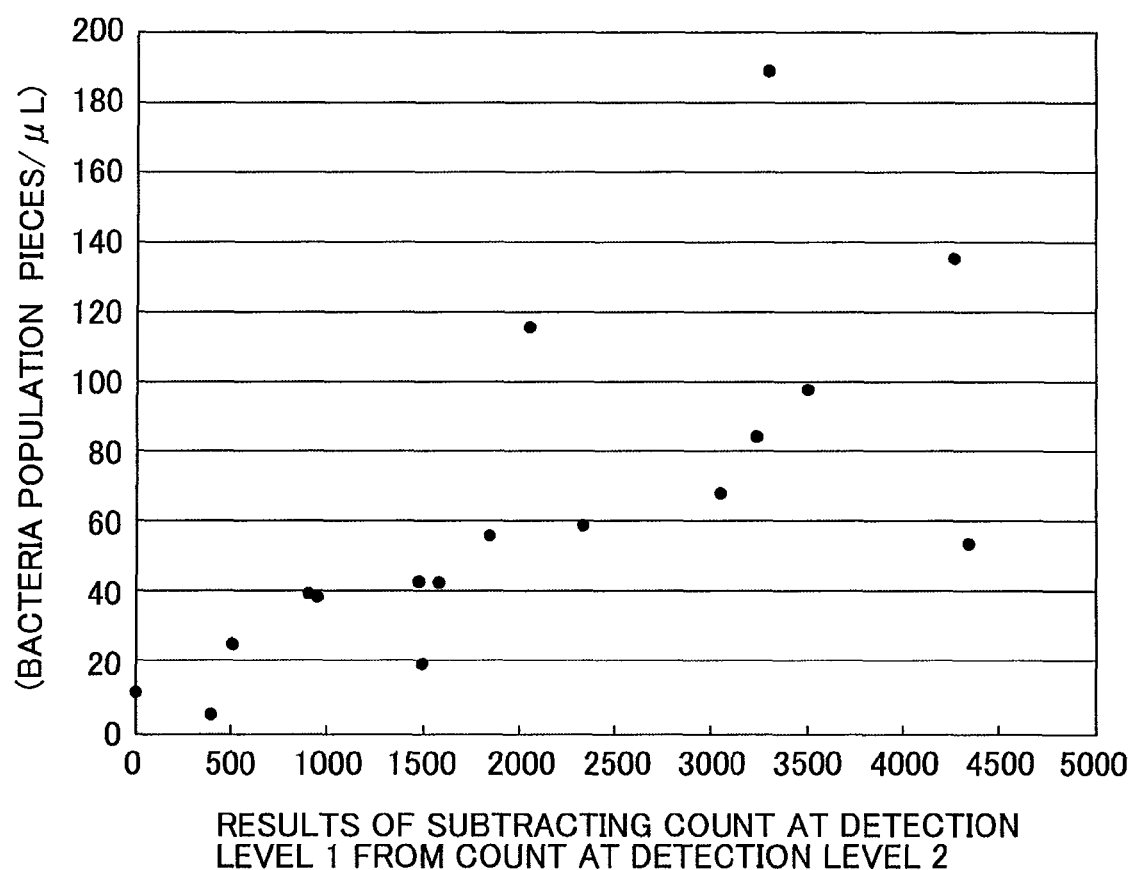
FIG. 10 is a diagram that graphically shows differential obtained by subtracting a particle count at detection level 2 from a particle count at detection level 1 in a sample which contained bacteria.

FIG. 10 represents the differential obtained by subtracting the particle count at detection level 2 from the particle count at detection level 1, in a urine sample that contained bacteria. As the bacterial concentration increases, the difference becomes more significant. This difference is considered to be the bacteria. Overall images of the samples in which bacteria are likely to appear can be left by setting a threshold value for the difference or ratio between the counts. In this way, although the imaging detection levels only constitute one condition, whether microparticles are present or absent can be assumed by counting the number of particles at each detection level.

Figure 11:
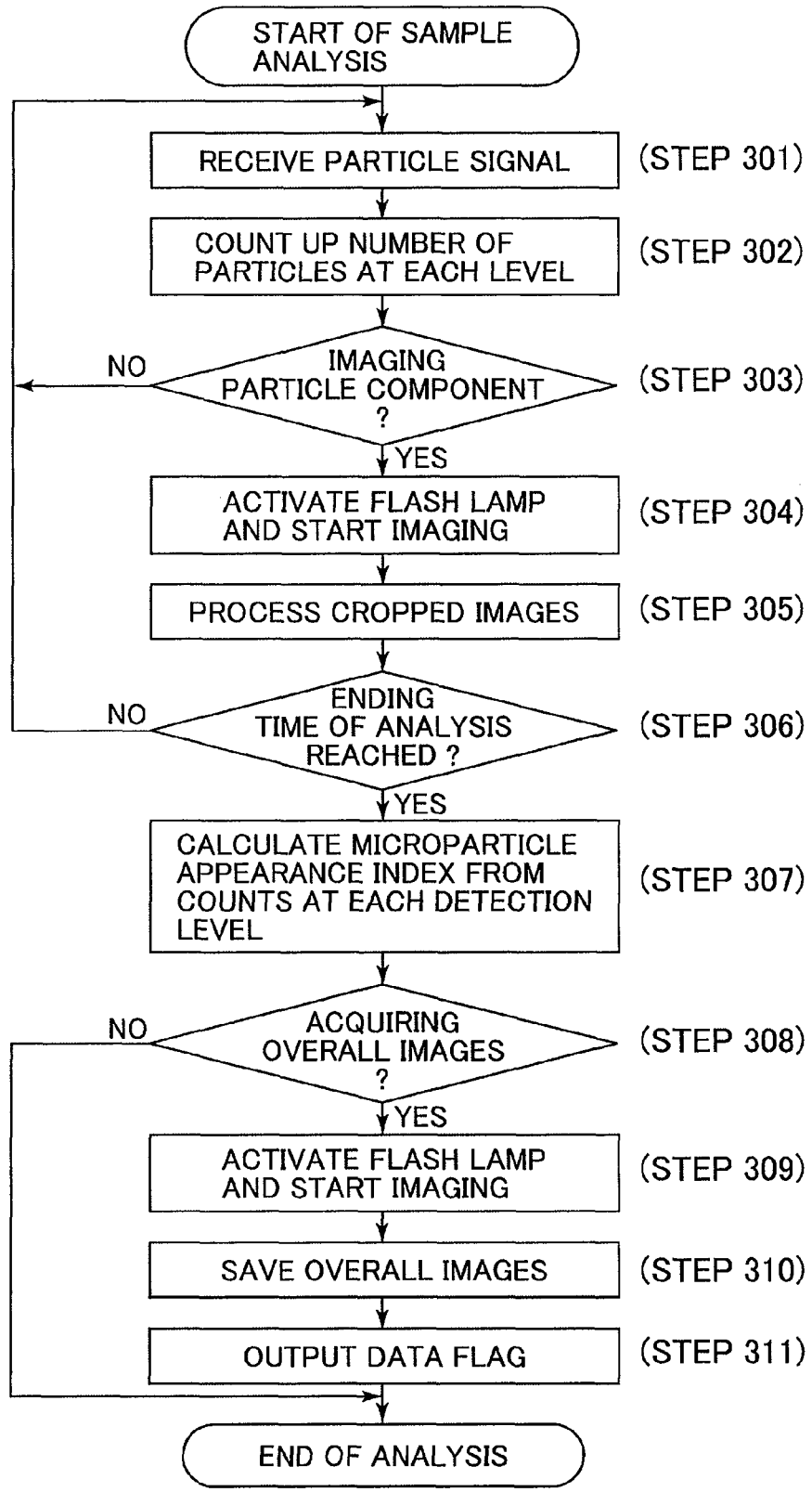
FIG. 11 is a diagram that explains a flow of a process for determining from the particle counts at each detection level whether overall images are to be acquired.

In addition, whether overall image acquisition is to be executed can be determined from the relationship between the detection counts at each level. FIG. 11 illustrates a flow of the process for determining from the particle counts at each detection level whether the overall image acquisition is to be conducted. Measurement is started and when particle components pass through a flow cell X, particle image signals are detected (Step 301). The number of particles at each of the detection levels (thresholds or higher) is counted (Step 302). For the particles exceeding one of the imaging detection levels, the flash lamp is activated and images acquired (Step 303). Particles below the imaging detection levels are excluded from imaging. Only component sections of all acquired particle images are cut and classified (Step 305). Upon an arrival of an ending time of the measurement (Step 306), the particle counts in Step 302 are compiled and the ratio between the counts at levels 1 and 2 or between the counts at levels 3 and 1 is calculated (Step 307). Whether the overall image acquisition is to be executed is judged from the relationship between the ratio and the counts (Step 308). If overall image acquisition of the sample is judged to be necessary, the flash lamp is activated and overall images are acquired (Step 309). After this, the image data is saved and a data flag is output (Steps 310 and 311). If the overall image acquisition of the sample is judged to be unnecessary, no image is acquired and the measurement completed.

Whether the overall image acquisition is to be conducted can also be set during particle detection count setting. For example, data is created and entered so that a desired particle count and a desired image number can be registered from the operating screen. The particle count and image number here refer to respectively, for example as shown in FIG. 12, five hundred particle counts derived by subtracting the count at detection level 2 from the count at detection level 1, and three overall images to be saved. The number of overall images to be saved can be set by setting either the detection count or the number of images to be acquired.

Other constituent elements of the present embodiment are substantially the same as those of the first embodiment, so that illustration and description of these elements are omitted.

In addition to providing substantially the same advantageous effects as those of the first embodiment, the second embodiment allows reduction in the memory capacity required for storage of overall images, and reduction in a reviewing time of the overall images.

Third Embodiment

Urine tests are based not only upon particle detection counts. Urinary chemical component analyses using a test paper method are also performed upon the sample. The results of these analyses have deep association with urinary sediment component analysis. Bacterial items, for example, are examined in the test paper method during the detection of nitrites, and the corresponding bacteria are measured on morphological measuring principles during urinary sediment tests.

In the test paper method, since small bacteria are not excluded, the sample exhibits a positive reaction for presence of all bacteria.

Measuring accuracy for bacteria and the like can therefore be enhanced by determining whether an overall image is to be acquired for each of positive test result items.

That is to say, when the urinary chemical analyses using the test paper method are also performed upon the sample, whether overall images are to be acquired and stored can be used as an assay criterion according to a configuration of the items for which the sample exhibited a positive reaction. The number of overall images to be saved can be set for each qualitative item, on the operating screen shown in FIG. 12.

Other constituent elements of the present embodiment are substantially the same as those of the first and/or second embodiments, so that illustration and description of these elements are omitted.

Fourth Embodiment

A fourth embodiment is described below using FIG. 13. During image display, an overall image of the imaging region and a cropped image of the imaging region differ in the image size itself, and when both images are simultaneously displayed on the display screen, the overall image of the imaging region may become downsized. If the entire imaging region is downsized, the operator will be unable to get a sense of size. For this reason, a size scale 403 is displayed in practically all screen modes to allow size discrimination.

FIG. 13 is a diagram that illustrates selection between a cropped image and an overall image of the imaging region, and enlarging/reducing functions. First, the cropped image is modified using the screen shown in section (A) of FIG. 13. This operation is equivalent to Step 101 in FIG. 6 or Step 201 in FIG. 7. Next, a select button 402 is pressed to change the screen to display of the imaging region overall image. Section (B) of FIG. 13 shows the display.

Both before and after the selection, the size scale 403 is constantly displayed on the screen. In the fourth embodiment of the present invention, one graduation in the scale 403 is equivalent to 10 micrometers. The scale 403 can be moved by mouse operations, for example. For further detailed observation of components too small to discriminate on the overall image of the region 409 shown in section (B) of FIG. 13, or for closer observation of an internal structure of a component, an enlarge button 405 is pressed to enlarge the image, as shown in section (C) of FIG. 13. Pressing a reduce button 406 returns the image to its original state shown in section (B) of FIG. 10.

Additionally, if the overall image of the region 409 is provided in plurality, a previous page button 407 and a next page button 408 are arranged for page changing. Pressing the select button 402 returns the screen to the display of the cropped image.

By carrying out these operations, the operator can move smoothly between the overall image and cropped image of the imaging region, and even if these images differ in size, the size of the scale 403 will follow, enabling smooth image observation free of any restrictions on screen display.

Other constituent elements of the present embodiment are substantially the same as those of the first and/or second embodiments, so that illustration and description of these elements are omitted.

DESCRIPTION OF THE REFERENCE NUMERALS

1 ... Flash lamp, 2 ... Field lens, 3 ... Microscope lens, 5 ... Objective lens, 6 ... Flash lamp driving circuit, 8 ... TV camera, 9 ... Beam of light, 11 ... Field stop, 12 ... Aperture stop, 15 ... Semiconductor laser source, 16 ... Collimator lens, 17 ... Cylindrical lens, 18 ... Reflecting mirror, 19 ... Micro-reflecting mirror, 20 ... Half mirror, 21 ... Stop, 22 ... Photodetection circuit, 23 ... Flash lamp activation control circuit, 24 ... Image memory, 25 ... Image-processing control circuit, 26 ... Feature extractor, 27 ... Identification unit, 28 ... Central control unit, 29 ... Review image memory, 30 ... Reference image memory, 31 ... Photodetection circuit, 32 to 35 ... Level detection circuits, 36 ... Duration measuring unit, 40 ... Particle analyzer, 50 ... Display unit, 60 ... Operating unit, 70 ... Imaging region, 80 ... Overall image of the imaging region, 90 ... Host computer, 91 ... Urinary qualitative analyzer, 100 ... Flow cell, 101 ... Imaging block, 102 ... Particle analyzing block, 103 ... Particle detection block, 104 ... Sheath fluid container, 105 ... Sheath fluid, 106 ... Syringe mechanism, 107 ... Nozzle, 108 ... Direct-sampling mechanism, 109 ... Sampling nozzle, 110a ... Sample, 110b ... Dye sample, 111 ... Dye solution, 112 ... Dyeing tank, 124 ... Flow circuit control unit, 281 ... Result-modifying processor, 282 ... Operational control unit, 283 ... Arithmetic processor, 284 ... Analytical result memory, 291 ... Overall-image memory, 292 ... Cropped image memory, 301 ... Selected region, 401 ... Review screen, 402 ... Image select button, 403 ... Size scale, 404 ... Item-dependent image window, 405 ... Enlarge button, 406 ... Reduce button, 407 ... Previous page button, 408 ... Next page button, 409 ... Overall image of the region

The invention claimed is:

1. A particle image analyzing method, comprising:
detecting particles flowing through a flow cell;
determining from a particle detection signal obtained whether desired particles are to be imaged, and then acquiring images of the desired particles;
storing an acquired overall image of a sample into an overall-image memory;
extracting particle components contained in the sample, and the number of the particles, from the acquired overall image of the sample;
analyzing the extracted particle components in accordance with feature parameters, then after classifying the particle components according to the kind of component, computing respective concentrations of the classified components, and storing the classified components with the computed concentrations into a cropped image memory;
displaying on display means the overall image stored in the overall-image memory; and
in accordance with to-be-added or to-be-changed particle component information entered from operating means, conducting modifications and concentration-modifying computations upon the components stored in the cropped image memory.

2. The particle image analyzing method according to claim 1, further comprising:
setting up a plurality of particle detection conditions each different from particle detection conditions used as an image acquisition trigger;
counting the number of particles detected independently under each of the conditions; and
in accordance with either the detection counts under each of the detection conditions, or a difference or ratio between the detection counts, determining whether the acquisition of overall images is to be executed and how many images are to be acquired, or whether the acquired overall image is to be stored into the overall-image memory and displayed.

3. The particle image analyzing method according to claim 2, further comprising:
in accordance with either the detection counts under each of the detection conditions, or a difference or ratio between the detection counts, cutting a part of an overall image as an image of particle components to be classified, and outputting a flag that indicates presence of small particle components not displayed.

4. The particle image analyzing method according to claim 1, further comprising:
identifying an internal region of the displayed overall image;
arithmetically modifying the number and concentration per unit volume based on the particle components and particle number information contained in the identified region; and
storing results into the cropped image memory.

5. The particle image analyzing method according to claim 1, further comprising:
storing into the cropped image memory any comment information entered from the operating means.

6. The particle image analyzing method according to claim 1,
wherein: the sample is a urine sample of an organism;
the urine sample is analyzed using a test paper method; and
whether the acquisition of overall images is to be executed, how many images are to be acquired, or whether the acquired overall image is to be stored into the overall-image memory and displayed, is designated in accordance with analytical results.

7. The particle image analyzing method according to claim 1, further comprising:
on the display means, displaying one of an overall image and cropped image of an imaging region selectively, and after redisplaying the displayed image in enlarged and reduced forms, displaying, in the overall image and cropped image of the imaging region, a size scale for discriminating a particle size in the displayed image.

8. A particle image analyzing apparatus, comprising:
means for detecting particles flowing through a flow cell, determining from a particle detection signal obtained whether desired particles are to be imaged, and then acquiring images of the desired particles;
an overall-image memory for storage of an overall image of a sample acquired by the imaging means;
a particle analyzer that extracts the number of particle components contained in the sample from the acquired overall image of the sample;
a feature extractor that extracts the particle components contained in the sample from the acquired overall image of the sample;
an arithmetic processor which, in accordance with feature parameters, analyzes the particle components extracted by the feature extractor, then classifies the particle components according to the kind of component, and computes respective concentrations of the classified components;
a cropped image memory for storage of the classified particle components and the concentrations thereof;
display means that displays the overall image stored in the overall-image memory;
operating entry means for entering particle component information to be added or changed; and
a result-modifying processor which, in accordance with the to-be-added or to-be-changed particle component information entered from the operating entry means, conducts modifications and concentration-modifying computations upon the components stored in the cropped image memory.

9. The particle image analyzing apparatus according to claim 8, further adapted to:
set up a plurality of particle detection conditions each different from particle detection conditions used as an image acquisition trigger;
count the number of particles detected independently under each of the conditions; and
in accordance with either the detection counts under each of the detection conditions, or a difference or ratio between the detection counts at each detection level, determining whether the acquisition of overall images is to be executed and how many images are to be acquired, or whether the acquired overall image is to be stored into the overall-image memory and displayed.

10. The particle image analyzing apparatus according to claim 9, further adapted to:
in accordance with either the detection counts under each of the detection conditions, or a difference or ratio between the detection counts, cut a part of an overall image as an image of particle components to be classified; and
output a flag that indicates presence of small particle components not displayed.

11. The particle image analyzing apparatus according to claim 8,
wherein: the result-modifying processor arithmetically modifies a concentration from the particle components and particle number information in the specific region identified from the operating entry means, and stores results into the cropped image memory.

12. The particle image analyzing apparatus according to claim 8,
wherein: the result-modifying processor stores into the cropped image memory any comment information entered from the operating entry means.

13. The particle image analyzing apparatus according to claim 8,
wherein: in accordance with analytical results obtained by analyzing a urine sample using a test paper method, the results being entered from the operating entry means, the result-modifying processor sets up whether the overall-image acquisition is to be executed for the sample and how many images are to be acquired, or whether acquired images are to be stored into the overall-image memory and displayed.

14. The particle image analyzing apparatus according to claim 8,
wherein: the result-modifying processor is adapted to display, on the display means, one of an overall image and cropped image of an imaging region selectively, then redisplay the displayed image in enlarged and reduced forms, and display, in the overall image and cropped image of the imaging region, a size scale for discriminating a particle size in the displayed image.

* * * * *